United States Patent
McMahon-Ayerst et al.

(10) Patent No.: US 6,610,901 B2
(45) Date of Patent: Aug. 26, 2003

(54) LEAKPROOF AND BREATHABLE UNDERGARMENTS AND SWIM WEAR

(75) Inventors: Marilyn McMahon-Ayerst, Lunenburg (CA); Doreen Clement, Lunenburg (CA); Brenda Maloney-Dawson, Lunenburg (CA)

(73) Assignee: Tri-Sis, Inc., Ontario (CA)

( * ) Notice: Subject to any disclaimer, the term of this patent is extended or adjusted under 35 U.S.C. 154(b) by 0 days.

(21) Appl. No.: 08/971,327

(22) Filed: Nov. 17, 1997

(65) Prior Publication Data

US 2002/0007171 A1 Jan. 17, 2002

Related U.S. Application Data

(63) Continuation-in-part of application No. PCT/CA96/00284, filed on May 9, 1996.

(30) Foreign Application Priority Data

May 16, 1995 (CA) .............................................. 2149477

(51) Int. Cl.$^7$ ........................... A61F 13/15; A61F 13/20
(52) U.S. Cl. ...................................... 604/378; 604/396
(58) Field of Search ........................... 2/400, 403, 406, 2/402, 401, 67, 82, 237, 238; 604/378, 396, 358, 365, 385.01; 442/86

(56) References Cited

U.S. PATENT DOCUMENTS

| | | | | |
|---|---|---|---|---|
| 3,397,697 A | * | 8/1968 | Rickard | 604/370 |
| 3,439,678 A | * | 4/1969 | Thomas | 604/372 |
| 3,989,867 A | * | 11/1976 | Sisson | 428/132 |
| 4,022,212 A | * | 5/1977 | Lovison | 604/395 |
| 4,194,041 A | | 3/1980 | Gore et al. | 428/315 |
| 4,302,853 A | * | 12/1981 | Mesek | 2/402 |
| 4,341,216 A | * | 7/1982 | Obenour | 604/370 |
| 4,411,660 A | | 10/1983 | Dawn et al. | 604/396 |
| 4,591,523 A | * | 5/1986 | Thompson | 428/131 |
| 4,609,584 A | * | 9/1986 | Cutler et al. | 428/156 |
| 4,614,000 A | * | 9/1986 | Mayer | 5/484 |
| 4,629,643 A | * | 12/1986 | Curro et al. | 428/131 |
| 4,690,681 A | * | 9/1987 | Haunschild et al. | 604/396 |
| 4,743,239 A | * | 5/1988 | Cole | 604/396 |

(List continued on next page.)

FOREIGN PATENT DOCUMENTS

| | | |
|---|---|---|
| CA | 1 157 601 | 11/1983 |
| CA | 2019474 | 4/1991 |
| CA | 2081058 | 4/1993 |
| CA | 1317536 | 5/1993 |
| CA | 1329864 | 5/1994 |
| DE | 9316248.0 | 3/1994 |
| EP | 0327823 A1 | 8/1989 |
| EP | 0627177 A1 | 12/1994 |
| WO | WO 92/12648 | 8/1992 |

Primary Examiner—Weilun Lo
Assistant Examiner—Michele Kidwell
(74) Attorney, Agent, or Firm—Jones, Tullar & Cooper, P.C.

(57) ABSTRACT

The present invention relates to a protective garment, which may be in the form of an undergarment or outerwear, such as a swimwear. The garment includes a body conforming portion for preventing leakage of body waste liquids. The garment includes, at least in the area of the garment which might come into contact with the body waste liquids, sheet material which comprises a lamination consisting of only two laminae. The first lamina is a liquid permeable fabric and the second lamina is a liquid impermeable but vapour permeable material. The liquid permeable fabric is positioned interiorly of the liquid impermeable but vapour permeable material having regard to the inside and outside of such a garment. Liquids are permitted to pass into and through the inner liquid permeable lamina to the interface between the inner laminae and liquid impermeable outer laminae whereat this liquid can be evaporated or dehydrated through the vapour permeable outer laminae.

22 Claims, 4 Drawing Sheets

U.S. PATENT DOCUMENTS

| | | | |
|---|---|---|---|
| 4,761,324 A | * 8/1988 | Rautenberg et al. | 428/198 |
| 4,813,950 A | * 3/1989 | Branch | 604/396 |
| 4,821,342 A | 4/1989 | Troyer | 2/82 |
| 4,840,841 A | * 6/1989 | Madsen | 428/286 |
| 4,868,928 A | 9/1989 | Norvell | 2/272 |
| 4,880,424 A | * 11/1989 | Rautenberg | 604/396 |
| 5,011,698 A | 4/1991 | Antoon, Jr. et al. | 126/395 |
| 5,098,419 A | * 3/1992 | Gold | 604/396 |
| 5,114,419 A | * 5/1992 | Daniel et al. | 604/385.1 |
| 5,155,867 A | 10/1992 | Norvell | 2/113 |
| 5,217,782 A | 6/1993 | Moretz et al. | 428/91 |
| 5,380,578 A | 1/1995 | Rautenberg | 428/172 |
| 5,631,074 A | * 5/1997 | Herlihy, Jr. | 442/35 |
| 5,804,021 A | * 9/1998 | Abuto et al. | 156/252 |
| 5,827,261 A | * 10/1998 | Osborn, III et al. | 604/387 |

\* cited by examiner

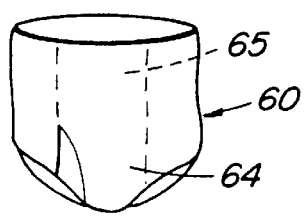
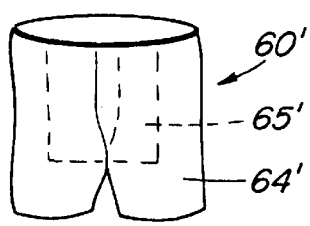
FIG. 9          FIG. 10          FIG. 11A
FIG. 11B
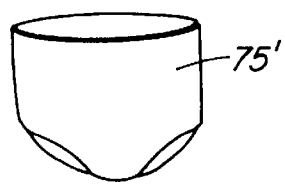
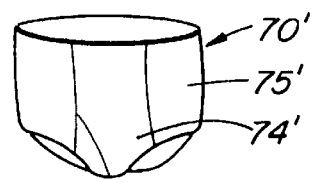
FIG. 12A          FIG. 12B
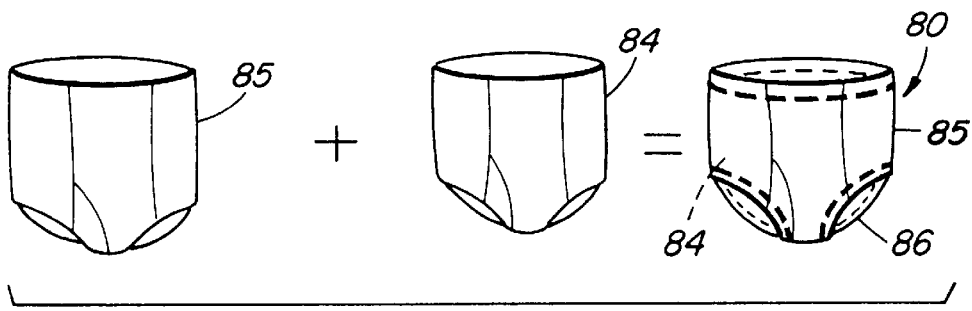
FIG. 13
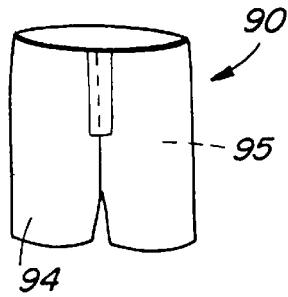
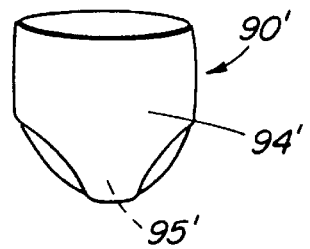
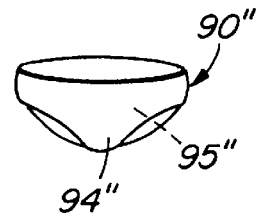
FIG. 14A          FIG. 14B          FIG. 14C

LEAKPROOF AND BREATHABLE UNDERGARMENTS AND SWIM WEAR

RELATED APPLICATION

This is a continuation-in-part of International Application No. PCT/CA96/00284, filed on May 9, 1996.

FIELD OF INVENTION

This invention relates to a protective garment which may be in the form of an undergarment or outerwear, and more particularly to a garment which includes a body conforming, lower torso portion for preventing leakage of body waste liquids. The garment may be a close fitting secondary garment to be worn over existing feminine protective means, and may be in the form of panties, briefs and underwear. Alternatively, rather than being in the form of an undergarment, the garment may be in the form of outerwear, such as swim wear or wear for other activities.

DESCRIPTION OF THE PRIOR ART

There are on the market numerous products designed for collecting and maintaining menstrual flow, and such products are designed for use with different magnitudes of flow. Leakages, which can cause embarrassing markings and/or troublesome cleanups, are still frequent occurrences. Moreover, there are periods of time when there is uncertainty as to whether light flow, not only menstrual flow when pads or tampon type products are not being worn, but discharge due to incontinence, or other causes, may occur.

An example of a bulkier form of product, provided for moisture management, as shown in EPO 0 627,177 A1, published 07.12.94, Moretz et al., is in the form of a suspended panel which includes a plurality of fabric layers, including at least a skin contacting layer, an intermediate fabric layer and an outer fabric layer. The panel is made to be used in addition to a garment which carries the panel.

In EPO 0327 823 A1, published 18.08.89, Darlington Fabrics Corporation, there is shown a simpler form of garment, but its structure differs from that of the present invention. In the structure of the product disclosed therein, an inner lamina of the lamination being used is a film which is breathable and liquid impermeable and an outer layer which is simply described as being a breathable fiber, typically knitted, which forms the body portion of the garment. Unlike the present invention, wherein the inner fabric lamina of the lamination forming the crotch area is liquid permeable, not water-resistant, and the outer lamina is liquid impermeable but breathable, the fluids gather on the inside of the inner lamina of the garment of this surface in the Darlington device. This has a disadvantage in that the collected fluids are subject to smearing and may produce a clammy feeling.

Yet other types of underwear has been proposed, such as that taught in U.S. Pat. No. 5,155,867, Oct. 20, 1992, Norvell. While utilizing layers of materials having different character, the garment of this reference is not designed to prevent the egress of body fluids from the wearer while maintaining the fluids within the garment in a state which does not provide discomfort to the wearer as in the present invention. Rather the Norvell design, which includes at least three layers, where two of the layers form a composite layer, provides protection to the wearer from contact with an external source of a fluid such as blood and other body fluids.

There is, therefore, a need for a protective garment which is capable of preventing leakage for body fluid flows which are not necessarily of great quantity and which can be worn either in combination with existing protective products or alone, and which is of a character providing comfort while not being conspicuous.

SUMMARY OF THE INVENTION

Basically, the present invention resides in a protective garment which includes a body conforming, lower torso portion for preventing leakage of body waste liquids, the lower torso portion being defined by sheet material and including a crotch portion disposed between a pair of leg openings. According to the present invention, the sheet material in at least the crotch area is a lamination consisting of only two laminae, a first of the two laminae being liquid permeable fabric, and a second of the laminae being liquid impermeable and vapour permeable material, at least one of the first and second laminae forming the lower torso portion above the crotch as well. The first lamina is an inner lamina fully occupying at least the crotch area for allowing passage of the liquids into the inner lamina. The second lamina is an outer lamina fully occupying at least the crotch area and being juxtaposed the inner lamina in the crotch area for preventing strike through to the exterior of the garment of the liquids from the inner lamina while allowing escape of vapour from the inner lamina.

BRIEF DESCRIPTION OF THE DRAWINGS

In the accompanying drawings, which show examples of garments incorporating the present invention.

FIG. 9 is a front view of men's briefs incorporating one form of the present invention;

FIG. 10 is a front view like FIG. 9 but showing the garment in the form of men's shorts;

FIGS. 11A and 11B illustrate the formation of one form of invention as incorporated in men's bikini style underwear;

FIGS. 12A and 12B illustrate components of men's briefs of a different embodiment then those shown in FIG. 9;

FIG. 13 illustrates the formation of yet a different form of men's briefs;

FIGS. 14A, 14B and 14C illustrate different embodiments of the invention as incorporated in three different styles of men's swimsuits.

DESCRIPTION OF PREFERRED EMBODIMENTS

Figure 1:
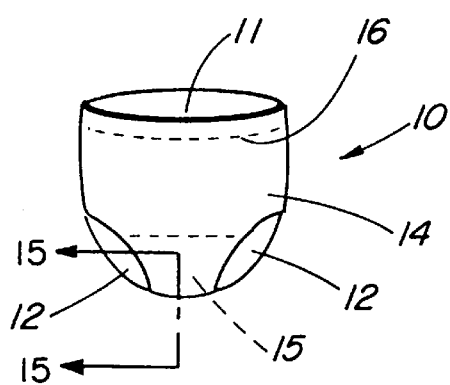
FIG. 1 is a front view of a female full panty according to the present invention.

Referring first to FIG. 1 there is shown a garment in the form of a full panty 10 for women's wear. This garment may have the appearance of an undergarment such as panties presently available for normal wear, but as it is designed to prevent the leakage of body wastes, such as menses. As will be apparent, although the garment may be worn over commercially available pads of tampons, it can also be worn as normal panties, particulary when there is believed to be the danger of light liquid flows occurring. The panty 10 is formed of material commonly termed sheet material and has the usual waist opening 11, and leg openings 12, between which is defined a crotch area 13. As will become apparent, while it is the characteristics of the sheet materials and the relationship of the elements in the sheet materials which make up applicants' invention, the garment would normally include, other elements such as elastic 16 to enhance the fitting characteristics.

The sheet materials defining the garment form a laminate at least in the crotch area 13 of only two laminae. A first lamina of the two laminae is in the form of a liquid permeable inner lamina 15 which may also be air permeable. It is shown in the form of a fabric gusset fully occupying the crotch area 13. A second lamina of the two laminae form an outer lamina 14 which is liquid impermeable but is breathable, i.e., it is air permeable so as to be capable of passing air and vapour therethrough. In the embodiment of FIG. 1, the outer lamina not only fully occupies the crotch area 13 juxtaposed the inner lamina 15, but also forms the remainder of the panty which is the lower torso conforming portion of this type of garment.

Figure 15:
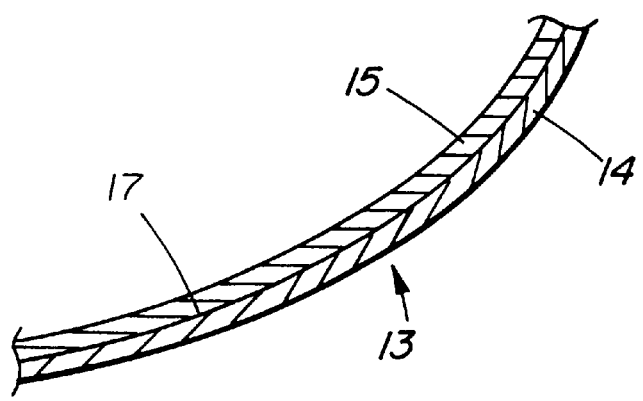
FIG. 15 is an enlarged cross sectional view as seen from the line 15—15 of FIG. 1.

Thus, in use, it can be seen that light body waste liquids whether they come initially into direct contact with the inside of the panty 10 or in effect leak from a pad or other devices being worn inside of the panty 10, can soak into the inner lamina 15, rather than smear on the inside of the panty. Such liquids may pass into and through this inner lamina 15 so as to contact an inner surface of the outer lamina 14 at interface 17 (FIG. 15). Because outer lamina 14 is liquid impermeable, the liquid does not exit the garment and thus does not produce exterior markings. However, because the outer lamina 14 is air permeable or breathable, vapour can pass outwardly through the outer lamina 14, thus resulting in some dehydration of the liquid held inwardly of the lamina. Thus, over a period of time, the garment can accommodate even a repeated or slow continuous application of the body liquid without resulting in an internal messy and uncomfortable smearing on the skin or the crotch 13 of the panty 10.

As to the type of materials used to provide the inner and outer laminae, the sheet material forming the inner lamina 15, must be liquid permeable. The lamina 15 may be in the form of a cotton gusset, and it may be detachable from the other lamina. However, while the material selected for inner lamina 15 may be woven and may be of various materials it may also be selected from materials which provide the above properties but are of the non-woven type. The sheet material for the outer lamina 14 must be selected from materials to provide the above described characteristics, which materials are also available in either woven or non-woven materials.

The inner lamina 15 may be formed of a thin, launderable, lightly absorbent material while the outer lamina 14 may be a thin, launderable, semipermeable membrane material. In the case where the protective garment is worn over existing feminine protective means, the wearer is protected from secondary flows of menstrual fluid from the existing feminine protection by the inner lamina 15 which absorbs any spots or light flows and by the outer lamina 14 which prevents any secondary flow liquid from striking through the garment while the vapour permeability of the semipermeable membrane permits vapour transfer across the garment so as to dry the secondary within the inner lamina 15.

The laminae 14 and 15 may be bonded, such as by adhesive or stitching in their juxtaposed relation. Alternatively, the inner and outer laminae may be connected together only at the periphery thereof.

Figure 2:
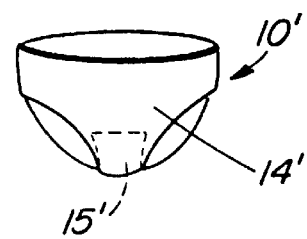
FIG. 2 is a view similar to FIG. 1, but showing a female bikini panty.

The garment shown in FIG. 2 is similar in fabrication to that of FIG. 1 in that it shows a female bikini panty wherein the overall body conforming lower torso portion forming the panty 10' is defined by an outer lamina 14' and there is inner an lamina which occupies the crotch area and may be provided by a gusset 15'. The properties of the materials forming the inner and outer laminae are the same as those described above.

Figure 3A:
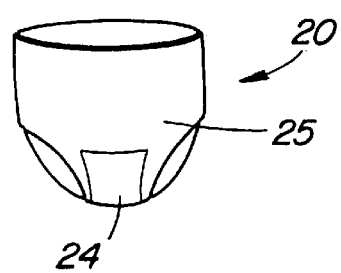
FIGS. 3A and 3B show front views of two different styles of female panties of a different embodiment of the invention than that of FIG. 1.
Figure 3B:
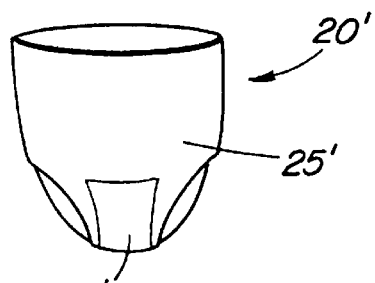

The embodiment of the panties 20 and 20' shown in FIGS. 3A and 3B differ in structure from that of FIG. 1 in that the inner lamina 25 and 25', which is liquid permeable, not only occupies the crotch area but forms the body portion of the panties. In the crotch area, the outer lamina 24 or 24' which is breathable and liquid impermeable is in the form of a gusset juxtaposed the outer surface of the inner lamina 25.

Figure 4:
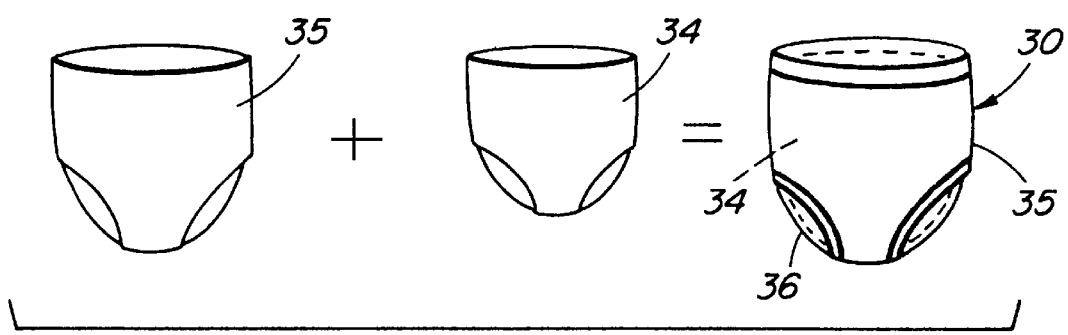
FIG. 4 illustrates the formation of a female panty of yet a different embodiment.

In the embodiment of FIG. 4, the inner and outer lamina together form the overall body encompassing, lower torso portion of the garment in the form of a women's panty 30. The inner lamina 35 is fitted within the outer lamina 34 and the two laminae are fastened together by exterior seams 36, the seams 36 preferably being sealed and liquid-proof.

Figure 5:
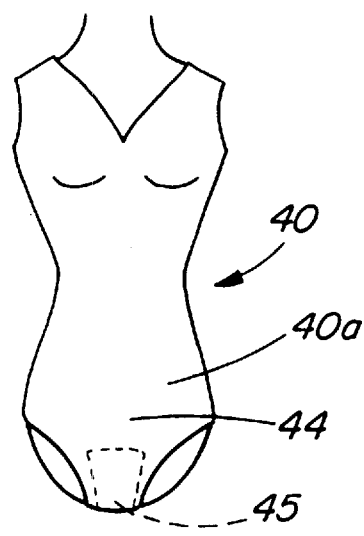
FIGS. 5 and 6 are front views of full female swim suits incorporating two different embodiments of the invention within such outerwear garments.
Figure 6:
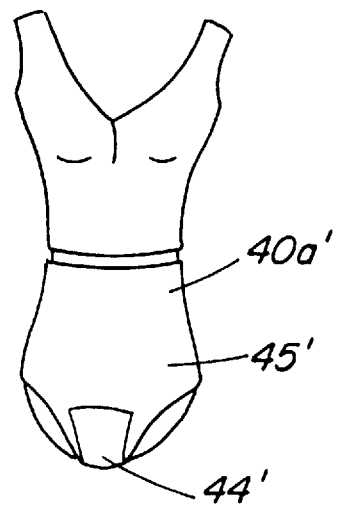

In the embodiment of the women's swim wear 40 shown in FIG. 5, the total outer garment is formed of the sheet material used to form outer lamina 44 which provides the lower torso portion 40a. The crotch is provided with an inner lamina 45 of the liquid permeable material previously described. In the swim wear of FIG. 6 the lower torso portion 40a' is formed of the same material as the outer lamina 45' and the lamina 44' is in the form of an exterior patch or gusset occupying the whole crotch area.

Figure 7:
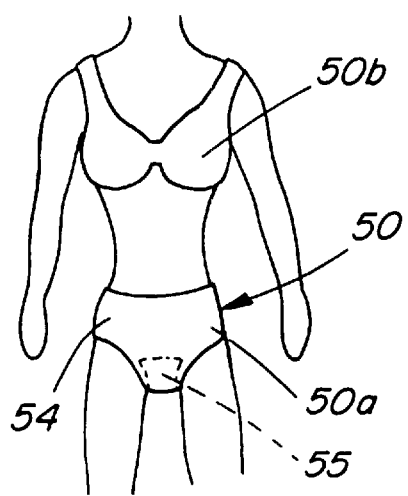
FIGS. 7 and 8 show front views of two different types of bikini swim wear as worn, and incorporating different embodiments of the invention.
Figure 8:
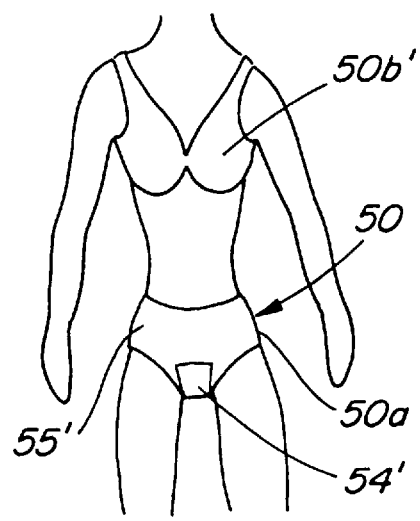

The bikini wear 50 of FIG. 7 includes a halter top 50b and a panty bottom 50a, and wherein the bottom 50a is formed of the outer lamina 54. The inner lamina 55 in the crotch portion of the bottom 50a is of the above described type of material for the inner lamina of the garment. In the bikini wear 50' of FIG. 8, outer lamina 54', which is the form of an outer patch on the exterior of the inner lamina 55' of the bottom 50a', the inner lamina 55' forms the lower torso portion forming the bottom 50a'.

In FIG. 9 there is shown men's brief's 60 which structurally correspond to that of panty 10 of FIG. 1, wherein the outer shell of the entire garment is formed by the material of the outer lamina 64 and thus it has an inner gusset or panel forming the inner lamina 65. While throughout the description there has been made reference to the lamination being formed in at least the crotch area, it would be normal to extend the lamination formed by the two laminae to a higher location as shown in the drawing in the front for men's wear. In that shown in FIG. 9 and other figures showing men's wear, the juxtaposed laminae may extend to the waist line. FIG. 10 shows a garment in the form of boxer shorts of the same type of lamination construction as that of FIG. 9. In the embodiment shown in FIGS. 11A and 11B, there is shown in FIG. 11A the inner lamina 75 forming the body conforming component of a men's bikini type underwear 70. In FIG. 11B, there is illustrated the finished product wherein an outer lamina 74 is applied to the crotch area and extending upward to the top thereof. FIGS. 12A and 12B show the formation of a regular style of men's briefs 70'. Using the same principle as FIGS. 11A and 11B brief 70' made up of inner lamina 75' with an outer lamina 74' only in the crotch and front area. The form of the men's brief.80 shown in FIG. 13 is of the same principle as that of the female panty of FIG. 4 and wherein the entire garment is formed of inner and outer lamina 84 and 85 respectively joined by seams 86.

In the three styles of men's swimsuits of FIGS. 14A, 14B and 14C, the boxer type 90, brief style 90' and the bikini style 90" are all formed in a manner depicted by the illustration of FIG. 13 in that the entire suits are of two laminae formed by the inner and outer laminae 95, 94; 95'94'; 95" and 94", respectively.

While the above describes the inner and outer laminae as being formed of initially separate laminae of sheet material, the same effect of the lamination provided after they are joined in juxtaposition as described above may be achieved by those skilled in the art by bringing together, during the forming of nonwoven materials, or in a weaving or knitting process, the materials of different character. In other words, in referring to the two laminae formed by an inner lamina and an outer lamina herein, such as lamina 15 and lamina 14, respectively, of FIG. 1, it should be appreciated that these laminae may not initially occur in separate sheets, but may be formed of materials having different characteristics as brought together in the forming of a more integral sheet.

What we claim is:

1. A protective garment including a body conforming, lower torso portion (10, 10, 20, 20', 30, 40, 50a, 50a', 60, 60', 70, 80, 90, 80' and 91') for preventing leakage of body waste liquids from a wearer, said lower torso portion being defined by sheet material and including a crotch area (13) disposed between a pair of leg openings, (12, 12) characterized by said sheet material at least in said crotch area being a lamination consisting of only two laminae, a first of said laminae (15, 15', 25, 25', 35, 45, 45', 55, 55' 65, 65', 75, 75', 85, 95, 95', 95") being a liquid permeable fabric material and a second of said laminae (14, 14', 24, 24', 34, 44, 44', 54, 54', 64, 64', 74, 74', 84, 94, 94', 94") being a liquid impermeable and vapour permeable material, at least one of said first and second laminae forming said lower torso portion above said crotch area as well, the first of said laminae being an inner lamina with respect to the wearer fully occupying at least said crotch area for allowing passage of said liquids into said inner lamina, the second of said laminae being an outer lamina with respect to the wearer fully occupying at least said crotch area and being juxtaposed said inner lamina in said crotch area for preventing strike through to the exterior of the garment of said liquids from said inner lamina while allowing escape of vapour from said inner lamina.

2. A close fitting garment as defined in claim 1, wherein said garment is selected from the group consisting of panties, briefs, underwear or undergarments and outerwear; characterized by said inner lamina being of thin, lightly absorbent material, said outer lamina being formed of thin material, whereby the wearer is protected from leakage of body fluids, by said inner lamina which absorbs any spots or light flows of said bodily fluids and by the outer lamina which prevents any liquid from said flows from striking through said garment, while said outer lamina allows vapour transfer across the garment resulting in dehydration of the liquid from said flows absorbed in said inner lamina so that the wearer is protected by the garment from said flows of said body fluids.

3. A garment in defined in claim 2, characterized by said inner and outer laminae being attached at seams, said seams being sealed and liquid-proof.

4. A garment as defined in claim 2, wherein said outerwear is swim wear.

5. A garment as defined in claim 1, wherein said garment is adapted to be worn as a secondary garment over existing feminine protective means, and is selected from the group consisting of panties, briefs, underwear or undergarments and outerwear, characterized by said inner lamina being formed of a thin, launderable, lightly absorbent material, and said outer lamina being a thin lamina formed of launderable semipermeable membrane material, whereby the wearer is protected from secondary flows of menstrual fluid from said existing feminine protective means, by the inner lamina which absorbs the secondary flows of menstrual fluid, and by the outer lamina which prevents any liquid from said secondary flows from striking through the secondary garment while vapour permeability of the semipermeable membrane material permits vapour transfer across the secondary garment thereby allowing the liquid from the secondary flows in said inner lamina to dry so that the wearer is protected by the secondary garment from secondary flows of menstrual fluids.

6. A garment in defined in claim 3, characterized by said inner and outer laminae being attached at seams, said seams being sealed and liquid-proof.

7. A garment as defined in claim 5, wherein said outerwear is swim wear.

8. A garment as defined in claim 1, characterized by said inner lamina and said outer lamina being bonded together by stitching or adhesive.

9. A garment as defined in claim 1, characterized by said inner lamina and said outer lamina being connected together only at peripheries thereof (36, 86).

10. A garment as defined in claim 1, characterized by said inner lamina being formed by a gusset member in the crotch area (15, 45, 55, 65, 65').

11. A garment as defined in claim 10 characterized by said member being detachable from a remainder of said garment.

12. A garment as defined in claim 1, characterized by said outer lamina being formed by a gusset member (24, 24', 44', 54', 74, 74').

13. A garment as defined in claim 12 characterized by said gusset member being detachable from a remainder of said garment.

14. A garment as defined in claim 1, characterized by said inner lamina being formed of a non-woven material.

15. A garment in defined in claim 14, characterized by said outer lamina being formed of a non-woven material.

16. A garment in defined in claim 15, characterized by said inner and outer laminae being attached at seams, said seams being sealed and liquid-proof.

17. A garment as defined in claim 1, characterized by said outer lamina being formed of a non-woven material.

18. A garment as defined in claim 1, characterized by said inner lamina being formed of a woven material.

19. A garment as defined in claim 18, characterized by said outer lamina being formed of a woven material.

20. A garment in defined in claim 19, characterized by said inner and outer laminae being attached at seams, said seams being sealed and liquid-proof.

21. A garment as defined in claim 1, characterized by said outer lamina being formed of a woven material.

22. A garment in defined in claim 1, characterized by said inner and outer laminae being attached at seams, said seams being sealed and liquid-proof.

* * * * *